(12) United States Patent
Archer et al.

(10) Patent No.: US 10,613,071 B2
(45) Date of Patent: Apr. 7, 2020

(54) CENTRIFUGE ENVIRONMENTAL CHAMBER

(71) Applicant: The Hong Kong University of Science and Technology, Hong Kong (CN)

(72) Inventors: André Archer, Hong Kong (CN); Charles Wang Wai Ng, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 264 days.

(21) Appl. No.: 15/425,501

(22) Filed: Feb. 6, 2017

(65) Prior Publication Data

US 2017/0227676 A1 Aug. 10, 2017

Related U.S. Application Data

(60) Provisional application No. 62/388,691, filed on Feb. 4, 2016.

(51) Int. Cl.
*G01N 33/24* (2006.01)
*G01N 15/08* (2006.01)

(52) U.S. Cl.
CPC ......... *G01N 33/24* (2013.01); *G01N 15/0806* (2013.01)

(58) Field of Classification Search
CPC .......................... G01N 33/24; G01N 15/0806
(Continued)

(56) References Cited

U.S. PATENT DOCUMENTS 3,633,419 A * 1/1972 Arita ..................... E02B 1/02
  73/148
4,328,676 A 5/1982 Reed
(Continued)

FOREIGN PATENT DOCUMENTS

CN 202548120 U 11/2012
CN 202762446 U 3/2013
(Continued)

OTHER PUBLICATIONS

Tristancho, J., Caicedo, B., Thorel, L., and Obregón, N. "Climatic Chamber With Centrifuge to Simulate Different Weather Conditions," Geotechnical Testing Journal, vol. 35, No. 1, 2012, pp. 159-171, https://doi.org/10.1520/GTJ103620. ISSN 0149-6115 (Year: 2012).*

(Continued)

*Primary Examiner* — Nathaniel J Kolb
(74) *Attorney, Agent, or Firm* — Saliwanchik, Lloyd & Eisenschenk

(57) ABSTRACT

The present invention includes an apparatus, method and centrifuge environmental chamber system for use in a centrifuge to induce different atmospheric paths as boundary conditions to a soil model during a centrifuge test. The invention is configured to be mounted on top of a strongbox, is based on a convection design principle, with components adapted for use in a centrifuge, and software for continuous control and data acquisition. An apparatus for a centrifuge environmental chamber can include a model strongbox including a model space, an airflow channel configured to pull air from the model space and push back the air to the model space, and a humidity nozzle placed in the model space.

25 Claims, 8 Drawing Sheets

(58) Field of Classification Search
USPC .......................................................... 73/865.6
See application file for complete search history.

(56) References Cited

U.S. PATENT DOCUMENTS

| | | | |
|---|---|---|---|
| 4,602,503 | A | 7/1986 | Hile et al. |
| 5,213,259 | A | 5/1993 | Stouffer |
| 5,302,023 | A | 4/1994 | Larsen et al. |
| 5,503,032 | A * | 4/1996 | Tikhtman ............... G01N 17/00 165/247 |
| 5,634,876 | A | 6/1997 | Schofield |
| 5,767,381 | A | 6/1998 | Konno et al. |
| 5,854,433 | A * | 12/1998 | Patel ..................... G01N 17/002 73/865.6 |
| 6,213,198 | B1 * | 4/2001 | Shikata .............. B60H 1/00478 165/202 |
| 7,686,285 | B2 | 3/2010 | Murray et al. |
| 8,240,157 | B2 | 8/2012 | Meyer et al. |
| 8,359,906 | B2 | 1/2013 | Shimada et al. |
| 8,418,491 | B2 | 4/2013 | Matsui |
| 2011/0061477 | A1 * | 3/2011 | Fitz ...................... G01N 17/002 73/865.6 |
| 2011/0117470 | A1 * | 5/2011 | Aras ................. H01M 8/04014 429/452 |
| 2018/0172303 | A1 * | 6/2018 | Conrad ............... F24F 11/0008 |

FOREIGN PATENT DOCUMENTS

| | | |
|---|---|---|
| CN | 203786570 U | 8/2014 |
| CN | 104075905 A | 10/2014 |
| CN | 203965169 U | 11/2014 |
| CN | 203965170 U | 11/2014 |
| CN | 204461978 U | 7/2015 |
| CN | 204710357 U | 10/2015 |

OTHER PUBLICATIONS

Castiblanco, PM et al., A new climatic chamber adapted to the mini-centrifuge for simulating soil drying, EUROFUGE 2016, $3^{rd}$ European conference on Physical Modeling in Geotechnics, Jun. 2016, submitted Aug. 31, 2016, pp. 111-115, Nantes, France, https://hal.archives-ouvertes.fr/hal-01358216.

Take, W.A. et al., An atmospheric chamber for the investigation of the effect of seasonal moisture changes on clay slopes, In: International Conference on Physical Modeling in Geotechnics, ICPGM '02, Jul. 10, 2002 to Jul. 12, 2002, St. John's Newfoundland, Canada pp. 765-770.

Zielinski, Marcin et al., Assessment of water retention behaviour in compacted fills, Proceedings of the Institution of Civil Engineers, Geotechnical Engineering, 2011, pp. 139-148, vol. 164 Issue GE2, ICE Publishing.

Matziaris, Vasileios et al., Centrifuge model tests of rainfall-induced slope failures for the investigation of the initiation conditions, Geophysical Research Abstracts, 2015, vol. 17, EGU2015-7727, EGU General Assembly.

Caicedo, B. et al., Centrifuge modeling of soil atmosphere interaction using a climatic chamber, Physical Modelling in Geotechnics, Springman, Laue & Seward (eds), 2010, pp. 299-305, Taylor & Francis Group, London.

Hudacsek, P. et al., Centrifuge modelling of climatic effects on clay embankments, Proceedings of the Institution of Civil Engineers, Engineering Sustainability, Jun. 2009, pp. 91-100, vol. 162, Issue ES2, ICE.

Tristancho, J. et al., Climatic chamber to model soil-atmosphere interaction in the centrifuge, 2008, pp. 117-121, Taylor & Francis Group, London, UK.

Tristancho, Julian et al., Climatic Chamber With Centrifuge to Simulate Different Weather Conditions, *Geotechnical Testing Journal*, Oct. 2011, 35(1):1-13, GTJ103620, www.astm.org, ASTM Int'l.

Song, Wei-Kang et al., Development of a Large-Scale Environmental Chamber for Investigating Soil Water Evaporation, *Geotechnical Testing Journal*, Sep. 9, 2013, 36(6):1-11, www.astm.org, ASTM Int'l.

Cui, Yu-Jun et al., Experimental and numerical investigation of soil-atmosphere interaction, Engineering Geology, 2013, pp. 20-28, vol. 165, www.elsevier.com/locate/enogeo, Elsevier Ltd.

Askarinejad, Amin, Failure mechanisms in unsaturated silty sand slopes triggered by rainfall, Doctoral Thesis, 2013, Diss Eth No. 21423, Abstract, ETH Zurich Research Collection, e-collection.library.ethz.ch/eserv/eth:7557/eth-7557-02.pdf.

Lozada, Catalina et al., Improved climatic chamber for desiccation simulation, E3S Web of Conferences, E-UNSAT 2016, 2016, pp. 1-6, vol. 9, 13002, EDP Sciences.

Askarinejad, Amin et al., Physical modelling of rainfall induced landslides under controlled climatic conditions, Eurofuge 2012, $2^{nd}$ Eurofuge Conference on Physical Modelling in Geotechnics, Deltares, Delft, The Netherlands, Apr. 23-24, 2012, published CD only, 10 pages.

Marshall, J. S. et al., "The Distribution of Raindrops With Size," *Journal of Meteorology*, Aug. 1948, 5:165-166.

Mason, B. J. et al., "Drop-size distributions from various types of rain," *Quarterly Journal of the Royal Meteorological Society*, 1960, 86(369):346-353.

* cited by examiner

CENTRIFUGE ENVIRONMENTAL CHAMBER

CROSS-REFERENCE TO RELATED APPLICATION

This application claims the benefit of U.S. Provisional Application Ser. No. 62/388,691, filed Feb. 4, 2016, which is herein incorporated by reference in its entirety.

BACKGROUND

Field

This disclosure concerns an environmental chamber, more specifically an environmental chamber for use in a geotechnical centrifuge that allows for continuous control of the relevant variables.

Background

U.S. Pat. No. 5,634,876 issued to Schofield, discloses centrifuges and associated apparatus and methods. Geotechnical centrifuge testing is a common advanced physical modelling method, used in the field of geotechnical engineering, to investigate the performance of geotechnical engineering related problems. Global soil behavior as well as fundamental soil parametric behavior is investigated with a geotechnical centrifuge. One of the advantages of using geotechnical centrifuge testing as a modeling tool is that "known" boundary conditions affecting soil behavior are applied and controlled, given that equipment is available to do this. It is therefore a necessary and continuous process to develop and design equipment that can be used in the geotechnical centrifuge environment. Such equipment should be able to accurately and reliably model desired boundary conditions, taking into account the principles of physics involved in such processes.

Of the various boundary conditions that can be controlled in a geotechnical centrifuge, the control of atmospheric boundary conditions is difficult due to the complex mass and heat transfer processes involved. Due to the increased interest in thermo-hydro-mechanical (THM) problems in geotechnical engineering, in particular problems involving soil-atmosphere interactions, focus has been placed on equipment that is able to reproduce such boundary conditions. Although it is more desirable to assess climate boundary conditions in real field conditions, limiting factors such as time, number of variables, not having control over the variables, etc. may lead to measurement uncertainty, reliability issues, and time consuming studies. Researchers using geotechnical centrifuge modeling have resorted to building instruments, referred to as climate, atmospheric or environmental chambers that are able to produce desired and well controlled atmospheric boundary conditions.

A number of geotechnical centrifuge facilities have developed environmental chambers to induce atmospheric boundary conditions, such as relative humidity, temperature, rain, wind and radiation. These systems make use of two types of operating principles; one is air control, more particularly a system where compressed air is circulated to create different boundary conditions, another is convection control, more particularly a system where fans are used to circulate air and induce boundary conditions. One important aspect of any environmental chamber, independent of the type of system employed, is that the chamber should be adiabatic; that is, a system where thermal equilibrium is attained and zero moisture loss occurs. The said environmental chambers are typically placed on a model strongbox; that is a box, typically constructed from aluminum able to withstand the centrifuge environment, in which the soil models are prepared. Each of the said operating principles can be used as a category to describe the different chambers in use; that is, convection control systems and air control systems.

Air control systems work on the principle that typically dry compressed air (i.e., low relative humidity) is circulated within the model space; that is, the space in the model strongbox in which the soil model is prepared. Heating elements can be installed at the air inlet of the air control system in order to increase the air temperature. Hydraulic atomizing spray nozzles, more specifically nozzles through which pressured water is forced to create a mist, are used to simulate rainfall conditions. Owing to the said adiabatic conditions, humidity increases in the model space to a maximum value of 100% when rainfall is induced, since no moisture can escape the model space. In addition to increasing the moisture in the air (i.e. relative humidity), spray from the rain nozzles will cause infiltration into a soil model rather than vapor diffusion. This shows that the rainfall devices are not suitable for relative humidity control. Relative humidity is decreased by the circulation of dry air, to a value dependent on the time of circulation and the relative humidity of the incoming air. This type of system is limited to only rainfall, maximum (i.e., 100%) and minimum (dependent on dry air input) relative humidity values, and temperature increase boundary conditions. Evidently, cooling is not possible with this system, and as such no cyclic temperature control is possible. In addition, wind and radiation control are not considered in air control systems.

An alternative to the air control system is a convection control system. This type typically consists of fans circulating air from the model space through a sealed channel and back into the model space. Fans in such a system refer to any device with rotating blades able to produce air flow in the desired direction. The air state is altered through psychrometric processes by means of heating or cooling elements placed in the sealed airflow channel, in the path of the airflow. Air is cooled or heated to produce a desired new air state. The heating or cooling elements refer to any solid state device capable of heating or cooling the air flowing past it. The altered air state is fed back to the model space where it mixes with the existing air to attain a desired atmospheric condition. This process normally alters only the relative humidity and temperature of the air and additional devices are required for rain, radiation and wind. Wind is typically altered by using variable speed fans that can increase or decrease air flow for varying wind speeds. Rain is typically simulated in the same manner as for the air control systems, by using the hydraulic atomizing spray nozzles for simulating rainfall conditions, more specifically nozzles through which pressured water is forced to create a mist, as described above, resulting in similar limitations. Radiation is simulated through the use of infrared (IR), ultraviolet (UV) and visible lighting to produce an irradiance spectrum close to that found in real atmospheric conditions. Tristancho et al. (2012) presented a convection control system. Successful use of the system at high-g conditions (where g is the Earth's gravitational acceleration) in the centrifuge environment was shown and the ability of such a system produce desired atmospheric boundary conditions. That said, limitations relating to the time required for changing the air state (i.e., the cycle time) and control of relative humidity as boundary condition exist. In addition, separate control of temperature and relative humidity as boundary conditions is not considered.

A limitation of both air- and convection control is the use of rain nozzles for relative humidity control. Nozzles are usually chosen considering rainfall characteristics with regard to drop size. When used for relative humidity control or during rainfall application a relative humidity value of 100% will be reached due to the hermetic model space and the drop size is also too large. Also, spray from rain nozzles will cause infiltration into a soil model rather than vapor diffusion associated with relative humidity.

In general, convection control systems are more versatile than air control systems since they can create and control various desired atmospheric boundary conditions. Convection control systems are designed using conventional air-conditioning design principles, scaled to be used in the centrifuge and modified to work in and withstand accelerated gravity conditions. As the needs and knowledge of researchers, not familiar with this area, increase alternative designs are required and continual improvements of current systems are pursued.

SUMMARY

The present invention is an apparatus, method and system for an environmental chamber to be used in a high-g centrifuge environment that allows diverse atmospheric paths to be induced efficiently as boundary conditions to a soil model. It is recognized by the present inventors that current centrifuge environmental chambers have not shown the capability of separate control of atmospheric paths and that extensive temperature and humidity cycle times are required.

The invention comprises a steel frame with sealed channels for air flow, cooling and heating units, fans and infrared and ultraviolet lights. In one embodiment of the present invention, a humidity nozzle is provided that enables change in the relative humidity of the air state by introducing water vapor mist into the system. Another feature of the embodiment is the fans that are installed to allow air flow in opposite directions through the channels. As part of the invention software connected to sensors and an instrumentation module is used to continuously measure and monitor variables related to the air state. The sensors used in the invention include temperature, relative humidity, wind speed and radiation sensors.

DETAILED DESCRIPTION

Overview

While the various embodiments used in the present invention are discussed in this description, it should be appreciated many relevant inventive concepts can be embodied in various specific contexts of the present invention. The specific embodiments discussed herein are merely illustrative of specific ways to make and use the invention and do not delimit the scope of the invention.

To facilitate the understanding of this disclosure, a number of terms are defined in the description. Terms defined herein have meanings as commonly understood by a person of ordinary skill in the areas relevant to the present disclosure. Terms such as "a", "an" and "the" are not intended as reference to only a singular entity, but may include the general class to which a specific entity refers. Terms for the specific embodiments described herein are merely for the purpose of the invention, however, their usage does not delimit the invention, except as outlined in the claims.

The term "prototype" used herein denotes the scaled relationship between the small-scale centrifuge specimen, referred to herein by the term "model", and an idealized large-scale structure or specimen in the nature. The scaled relationship is achieved by subjecting the model to a centripetal acceleration equal to N-times the Earth's gravity "g", hence it is said the model is at high-g conditions.

The present invention is an apparatus, method and system to simulate diverse atmospheric conditions in a high-g centrifuge environment. As mentioned, the system is a centrifuge environmental chamber. The environmental chamber is used to induce different atmospheric paths as boundary conditions to a soil model during a centrifuge test.

The present invention provides a system having a centrifuge environmental chamber adapted for use in a centrifuge and software for control and data acquisition. The software may be used to detect the atmospheric variables and control the various embodiments of the environmental chamber to induce a change in the air state. The software may be installed on a computer, connected to the environmental chamber and be able to store data (internally or externally), and also display or print data. The software is also used to continuously measure and/or monitor various parameters of the environmental chamber, e.g. relative humidity 22, air temperature 21, fan speed, heating and cooling element temperature, wind speed and radiation.

An environmental chamber based on convection control generally comprises fans, lights, heating and cooling units, and rain nozzles used in combination to produce various atmospheric conditions (i.e. temperature 21, relative humidity 22, radiation, rain and wind). The designs aim to change the state of atmospheric air through psychrometric processes. The disclosed environmental chamber has solid state (i.e. no movable parts) heating and cooling units for use in the centrifuge.

Figure 3:
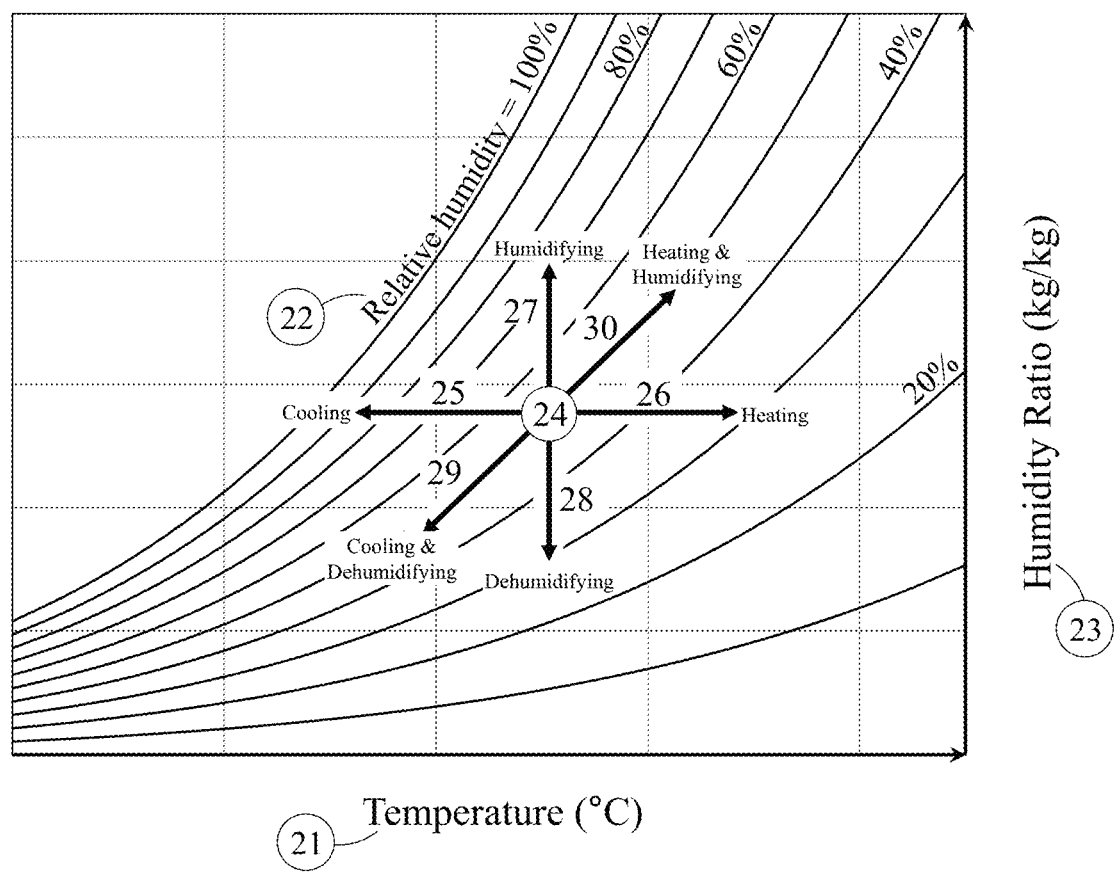
FIG. 3 is a schematic diagram showing a psychrometric chart indicating different psychrometric processes used to alter the air state during the use of the disclosed centrifuge environmental chamber.

FIG. 3 is a schematic of a psychrometric chart indicating various psychrometric processes. Psychrometric processes refer to the process of obtaining desired values of relative humidity 22 and air temperature 21 by changing the psychrometric properties of air (i.e. conditions of the atmosphere). The processes include heating 26 (i.e., raising the temperature), cooling 25 (i.e., lowering the temperature), dehumidification 28 (i.e., removing moisture from the air), and humidification 27 (i.e., adding moisture to the air). These processes usually work in combination, such as heating-and-humidification 30 or cooling-and-dehumidification 29, to produce a desired change in air state. Referring to FIG. 3, the different axes present psychrometric properties and in this disclosure the properties concerned are relative humidity 22 (in units of %), air temperature 21 (in units of ° C.) and humidity ratio 23 (in units of kg/kg). These properties are changed according to one of the processes indicated and, accordingly, the atmospheric state is altered. If an air temperature 21 value is known and a specific relative humidity 22 is desired, the humidity ratio 23 provides the water that should be added to or removed from the current air state to obtain said relative humidity 22.

Figure 1:
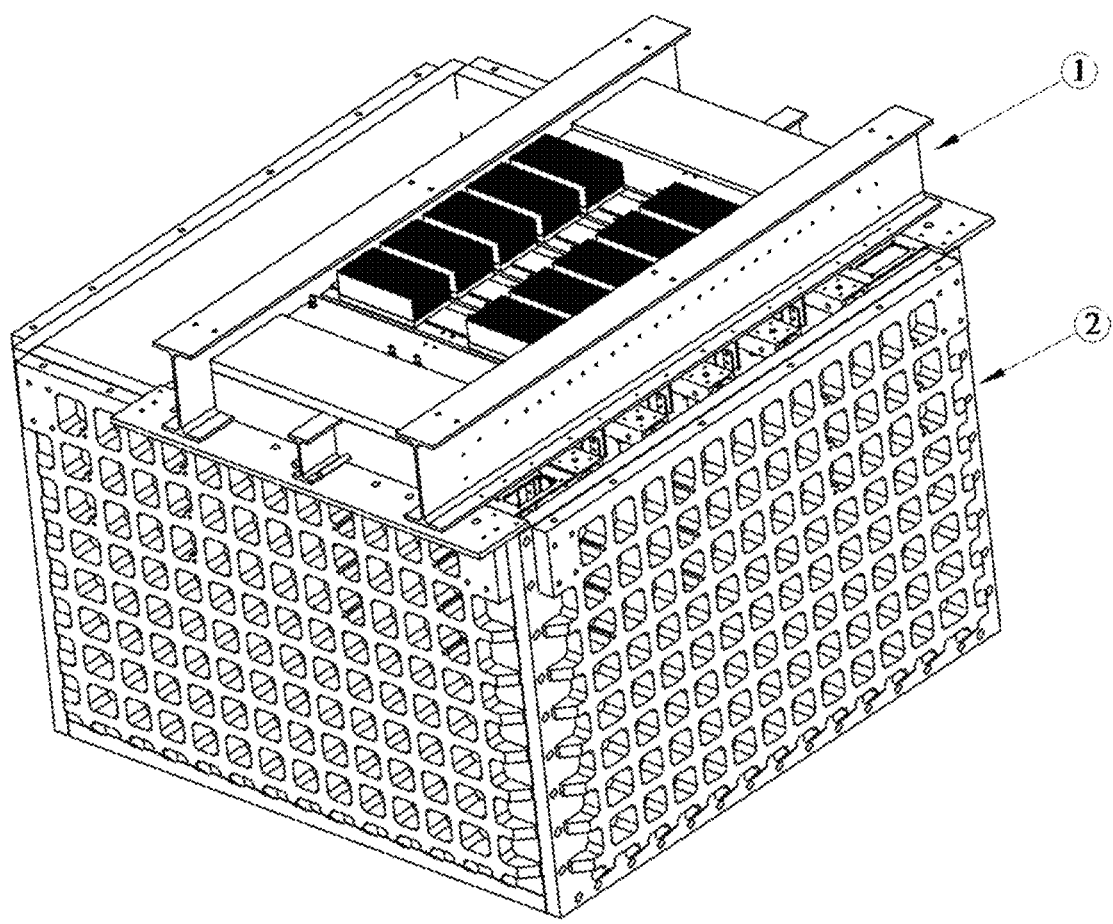
FIG. 1 is a perspective view of the complete assembly of the disclosed environmental chamber as fastened to the model strongbox.
Figure 2:
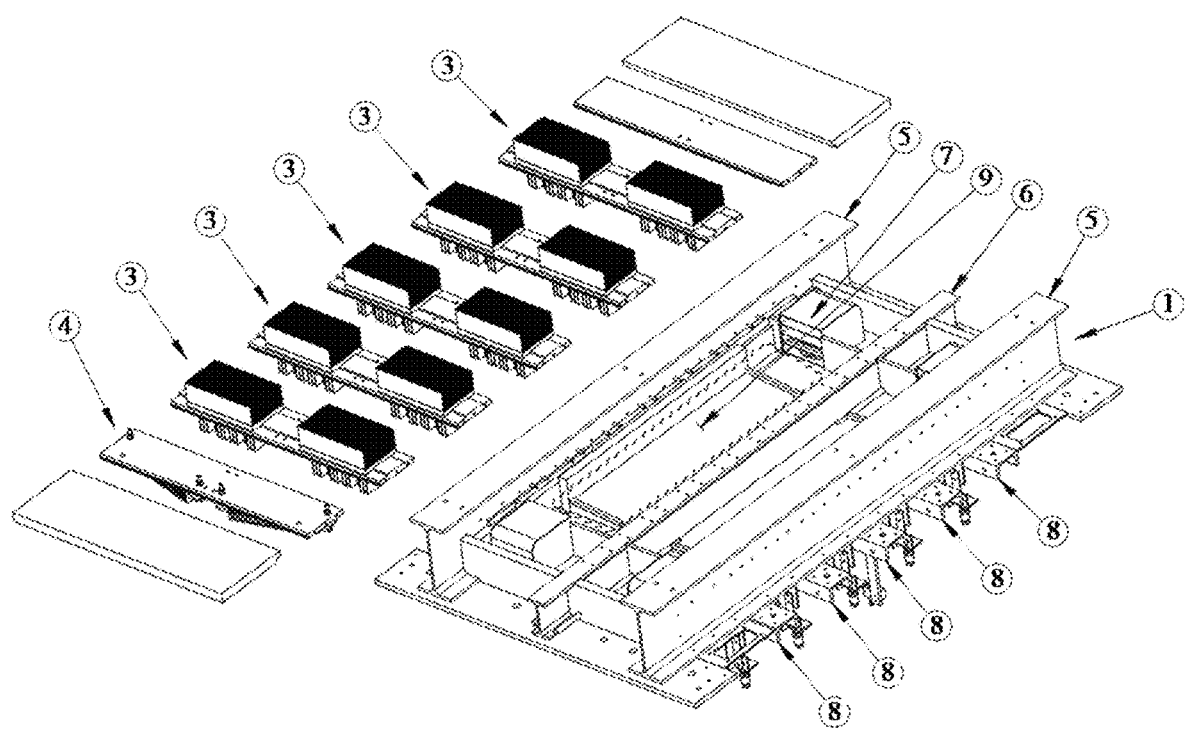
FIG. 2 is an exploded perspective view showing the components of the disclosed centrifuge environmental chamber.
Figure 4:
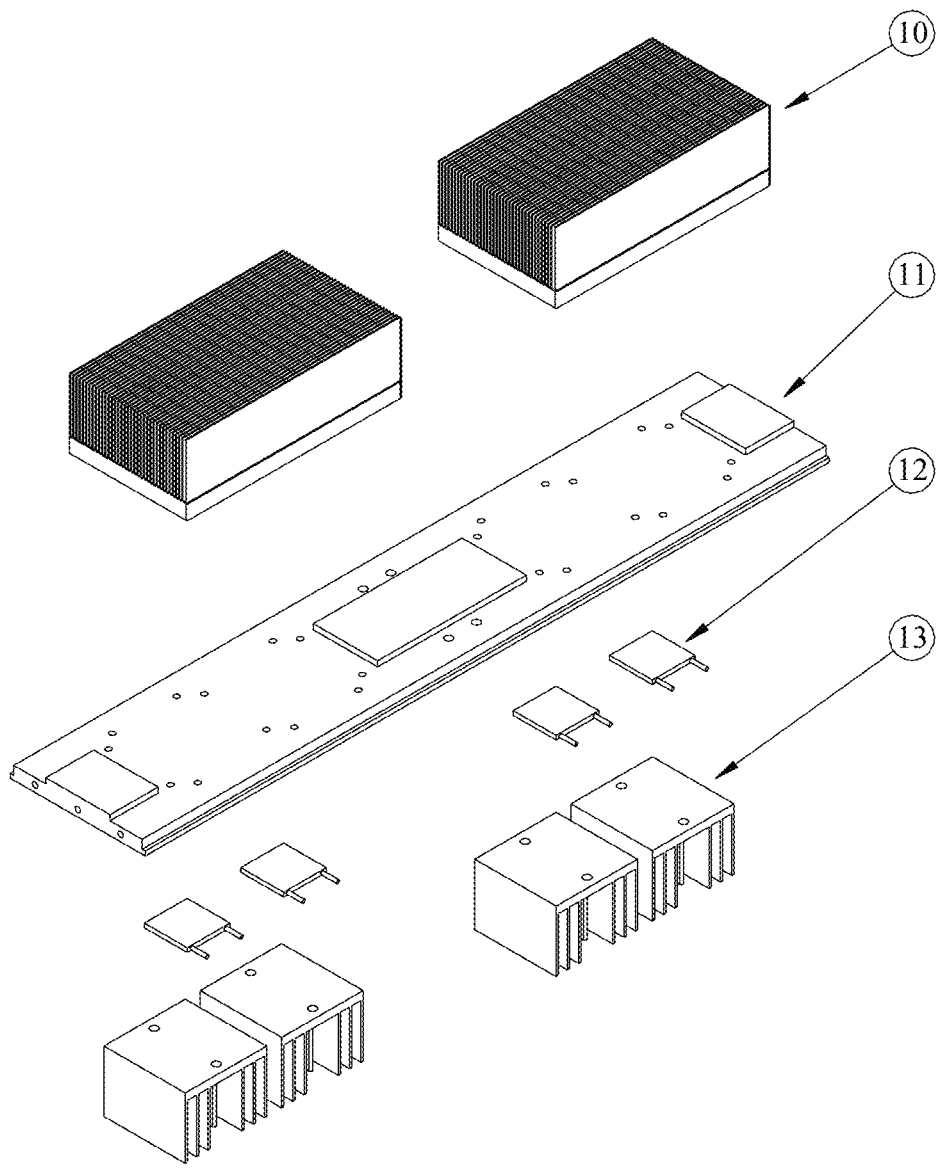
FIG. 4 is a perspective view showing the exploded components of the cooling unit used in the disclosed centrifuge environmental chamber.
Figure 5:
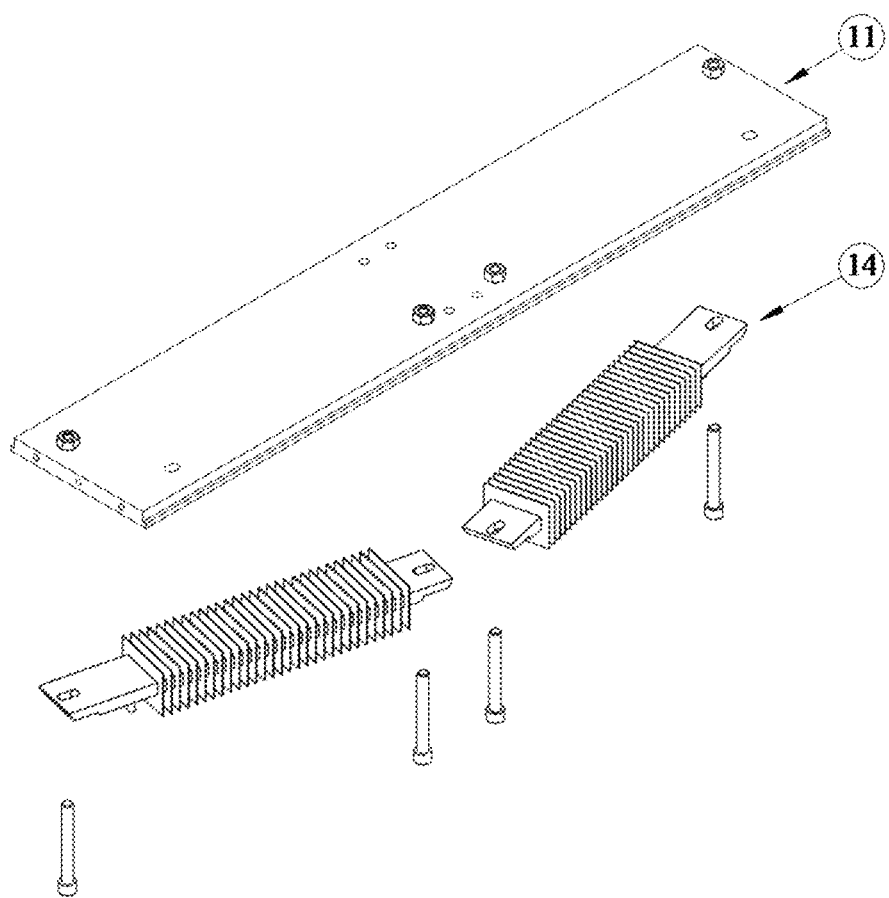
FIG. 5 is a perspective view showing the exploded components of the heating unit used in the disclosed centrifuge environmental chamber.

Referring to the disclosed environmental chamber in more detail, FIG. 1 shows a perspective view of the complete environmental chamber 1 and FIG. 2 shows an exploded perspective view of the environmental chamber 1, indicating the heating unit 4 and cooling unit 3. In this disclosure the environmental chamber body is constructed from two large steel I-beams 5 (200×100×5 mm), one smaller steel I-beam 6 (100×50×5 mm) and steel c-channel sections 8 (75×40 mm), all welded together as depicted in FIG. 2. Also shown in FIG. 2 is what is referred to in this disclosure as the airflow channels 9 within the environmental chamber 1. The heating unit 4 comprises any solid state heating element able to fit in the airflow channels 9 and capable of increasing the air temperature 21. In this embodiment the heating element comprises a finned strip aluminum heater 14 shown in FIG. 5, which depicts an exploded view of the heating unit 4 in FIG. 2. Cooling elements in this disclosure comprise any solid state cooling element able to fit in the airflow channels 9 and capable of reducing the air temperature 21. In this disclosure cooling elements comprise finned heat sinks 13 cooled down by means of Peltier plates 12 shown in FIG. 4, which depicts an exploded view of the cooling unit 3 in FIG. 2. The fins of the finned heat sinks 13 of the embodiment comprise micro-grooves for more efficient cooling by ensuring better heat transfer between the finned heat sinks 13 and air passing them. Heat dissipating heat sinks 10 are placed on the outside of the environmental chamber 1, above the aluminum flat plates 11 to dissipate heat from the Peltier plates 12. In both heating 4 and cooling 3 unit assemblies the various elements are fastened to 10 mm thick aluminum flat plates 11 (FIG. 4 and FIG. 5) which are fastened to the large- and small I-beams 5 and 6.

Figure 6:
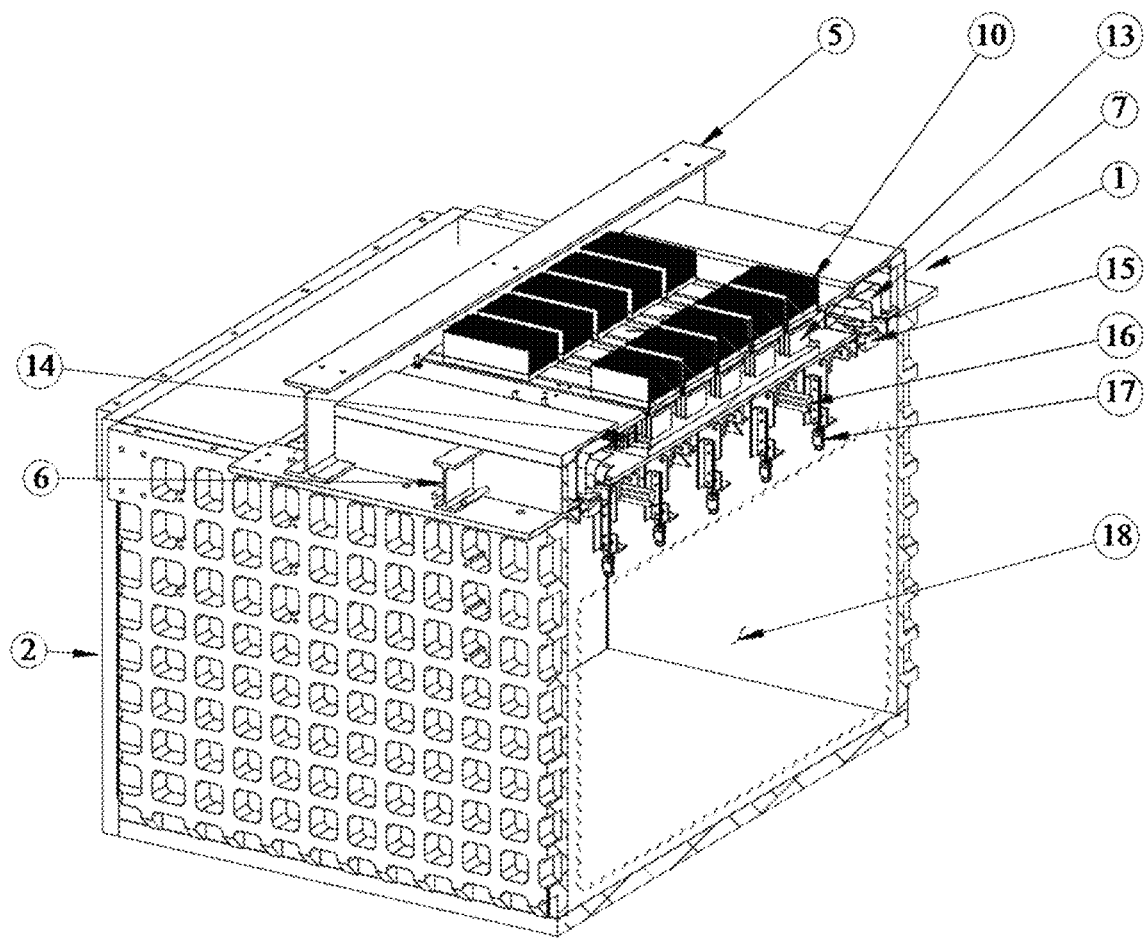
FIG. 6 is a cross sectional perspective view of the disclosed centrifuge environmental chamber.
Figure 7:
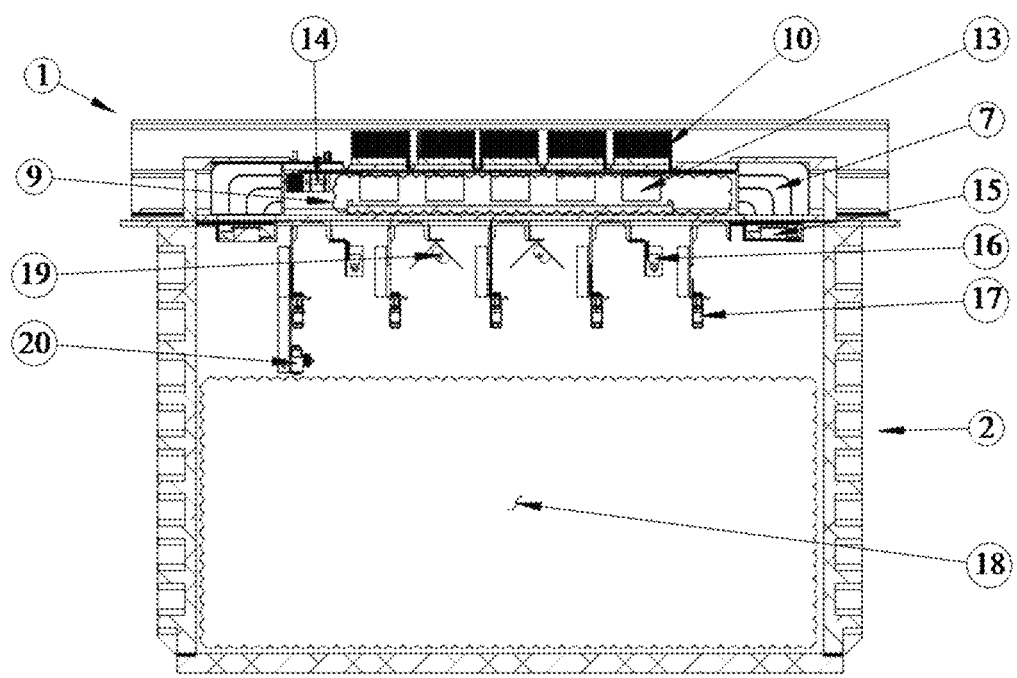
FIG. 7 is an elevation view of the cross sectional perspective view depicted in FIG. 6.

Referring now to FIG. 6, a cross-sectional perspective view of the environmental chamber 1 on top of a model strongbox 2, the model space 18 is shown of which the atmospheric state is changed. FIG. 7 shows an elevation view of the cross-sectional perspective view of the environmental chamber 1 in FIG. 6. In further detail, FIG. 7 depicts a humidity nozzle 20 placed inside the model space 18.

One significant aspect of the disclosed technology is the addition of the humidity nozzle 20 to overcome the shortcomings of current designs, which typically only include nozzles for rainfall 17 (FIG. 7) or rely on the heating 4 and cooling 3 units alone to induce humidity changes. Rain nozzles typically used have a mean drop diameter ranging from 30 µm to 60 µm, which is equivalent to light- and heavy rain at prototype scale (applying scaling laws for linear dimensions) and does not correspond to vapor size particles when referring to humidity. The humidity nozzle introduced in this disclosure has a mean drop size of 6 µm, which if scaled to prototype conditions equates to vapor size particles associated with humidity. In this disclosure nozzle 1/4J-SS-SUF1-SS from Spray Systems Inc. was used, however, any atomizing misting nozzle able to produce vapor size droplets conforming to humidity conditions can be used as the humidity nozzle 20.

Another feature of the embodiment is the fans 15 shown in FIG. 7, which are installed to produce air flow in opposite directions through the airflow channels 9. That is, fans on opposite sides of the chamber are installed to pull air from the model space 18 and feed it into the airflow channels 9 passing the heating 4 and cooling 3 units, and the air is pushed back into the model space 18 at the other end. This allows for a more efficient system where, depending if a heating or cooling process is set, either cold air or hot air can directly be fed into the model space 18. Air is directed into an airflow channel 9 by means of a directional air scoop 7 with turning vanes mounted on top of the fan 15. For this disclosure the fans 15 comprised 120 mm×120 mm axial fans with variable speed control.

An important aspect of the disclosed centrifuge environmental chamber 1 is that during use the environmental chamber 1 assembly should be completely sealed form the external environment. Moreover, insulation should be used to shield the various embodiments from external atmospheric conditions. For this disclosure waterproof silicone sealant (not shown) and extruded polystyrene foam boards (not shown) are used to seal and shield the centrifuge environmental chamber.

A typical test procedure of the disclosed environmental chamber includes the following steps:
 (1) Ensure the environmental chamber 1 is properly fastened to the model strongbox 2, appropriately sealed and properly placed on the centrifuge swing arm;
 (2) Ensure all essential electrical connections and software are in working order;
 (3) Spin the centrifuge to a selected centrifuge acceleration level;
 (4) Commence measurement of the average initial atmospheric state in the model space by means of the relative humidity 22 and temperature 21 sensors (not shown);
 (5) Select a desired atmospheric condition, after which the heating 4 and cooling 3 units as well as humidity nozzle 20 are switched on as required to obtain the desired atmospheric condition. The specific sequence of switching the units on and off is based on the desired condition and the configuration within the environmental chamber 1.
 (6) Continuously measure and observe the atmospheric state while ensuring the desired state is obtained, where after the last on and off configuration of the components can be maintained to keep the atmospheric condition stable.
 (7) If a new atmospheric condition is desired, the final atmospheric state achieved in step (6) is the new initial state and the process is repeated from step (5).

The test procedure of the disclosed enviornmental chamber is the same at different centrifuge accelerations. During the process the fans 15 are continuously on to ensure circulation and more importantly pull the air from the model space into the environmental chamber airflow channels 9 to change the state of the air. Variable speed fans, as used in this disclosure, are used to induce different wind speeds which can be measured using an anemometer (not shown). If an increase in air temperature 21 by means of radiation heating is desired, infrared 19, ultraviolet lights 16 and visible lighting (not shown) may be used. Moreover, if rainfall is desired the rain nozzles 17 can be used, connected to a pressurized water tank (not shown) which will force water through the nozzles creating rain conditions during the test. The characteristics (i.e. rainfall intensity and duration) of the rainfall are dependent on the rain nozzle 17 properties and applied pressure, which should be obtained from the manufacturer. In this disclosure nozzle LNN 1/4J-1.5 from Spray Systems Inc. was used as the rainfall nozzle 17. It should be noted that by employing any of the aforementioned external elements to change the air temperature 21, relative humidity 22, rainfall, and wind speed, the atmospheric state will change, after which a new initial state will be established and the typical procedure can be followed to obtain a new desired atmospheric state.

EXAMPLES

FIG. 3 depicts a psychrometric chart with various psychrometric processes. An arbitrary initial atmospheric state is shown, which can be changed by adopting one of the psychrometric processes indicated. The psychrometric processes involve either heating or cooling for air temperature 21 change, or an increase or decrease of the moisture in the air to change relative humidity 22. These processes ordinarily occur simultaneously since air temperature 21 and relative humidity 22 are affected by each other.

The heating 4 and cooling 3 units are used for the purpose of air temperature 21 change, however this will also result in a change in the relative humidity 22. During heating the air will dry out as the moisture in the air evaporates, decreasing the relative humidity 22. During cooling, if the cooling units are below the dew point for the current air state, condensation will occur on the finned heat sinks 13, which will extract moisture from the air (i.e. water droplets will form on the finned heat sinks 13), and also decrease the relative humidity 22. Due to the gravity, condensed water will drip from the finned heat sinks 13. Sloping channels (not shown), placed underneath the finned heat sinks 13, may be used to channel water away. Drained water can be further channeled to drainage pipes (not shown) connected to collection containers (not shown), where it can be monitored if required. If the air is cooled down with the cooling elements above the dew point temperature for the current air state, no condensation will occur on the finned heat sinks 13, hence no moisture is extracted from the air (i.e. no water droplets will form on the heat sinks 13), and no decrease in relative humidity 22. Cooling above dew point temperatures however, will result in a longer time required for cooling since the temperature difference between the air state and the cooling units 3 is less.

By addition of the humidity nozzle 20 into the system, water vapor is added as required to reach a desired relative humidity 22 value, additionally it is used to maintain a constant relative humidity 22 value by adding water vapor when moisture is extracted from the air during heating or cooling as explained above.

Figure 8:
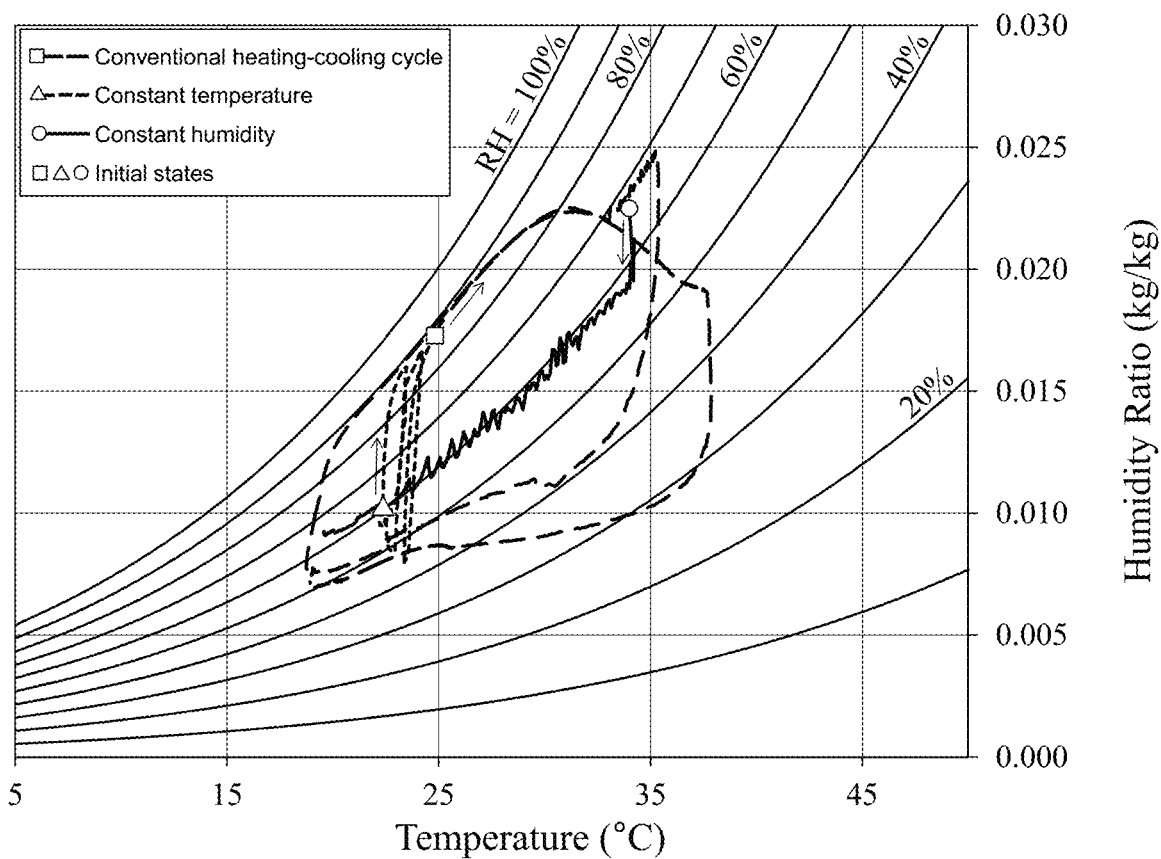
FIG. 8 is shows atmospheric paths measured during a centrifuge test using the disclosed centrifuge environmental chamber.

In order to demonstrate the performance of the disclosed centrifuge environmental chamber 1, a centrifuge test was carried out at 40 g (i.e. 40 times the Earth's gravity). FIG. 8 depicts the measured atmospheric paths obtained during the centrifuge test. It is demonstrated that under elevated gravity conditions, the environmental chamber 1 is capable of producing various climate conditions.

A test with a conventional atmospheric path, in which no specific atmospheric variable is controlled and assuming heating first, may be conducted by: i) placing the environmental chamber affixed to the model strongbox (ensuring a proper seal) in the centrifuge swing arm (not shown), ii) spinning the centrifuge to the desired gravitational acceleration, iii) switch on the fans 15 to ensure air flow in the direction for heating, iv) assess the initial atmospheric state of the model space using air temperature 21 and humidity sensors (not shown), v) switch on the heating unit 4, allowing the air temperature 21 to increase to the desired value, vi) after reaching the desired air temperature 21 and maintaining the conditions for a desired time period, switch off the heating unit 4 and switch on all the cooling units 3, vii) switch off the fans 15 for heating air flow and switch on the opposite fans 15 for air flow in the direction of cooling and allow for the air to cool down, viii) after reaching the desired air temperature 21, repeat the process for heating/cooling cycles from step 'v' bearing in mind to change the fans 15 as required. During the aforementioned process the air state is continuously monitored.

Similar to the process in of the test with a conventional atmospheric path, a test with a constant relative humidity 22 atmospheric path is performed with the addition of using the humidity nozzle 20. During the heating/cooling cycles the humidity is maintained at a desired value by adding moisture to the air as desired with humidity nozzle 20, due to the fact that moisture will be extracted from the air as described above when the heating 4 and cooling 3 elements are used for the purpose of air temperature 21 change.

A test with a constant air temperature 21 atmospheric path where relative humidity 22 is increased or decreased may be conducted by: i) placing the environmental chamber affixed to the model strongbox (ensuring a proper seal) in the centrifuge swing arm (not shown), ii) spinning the centrifuge to the desired gravitational acceleration, iii) switch on the fans 15 to ensure air flow in any direction, iv) assess the initial atmospheric state of the model space using the temperature and humidity sensor (not shown), v) switch on the heating units 4 and required number of cooling units 3 to a combination that produces the desired constant air temperature 21 (i.e. for higher air temperatures 21 the heating unit 4 will be warmed with less cooling units 3 on, and for lower air temperature 21 vice versa), allowing the air temperature 21 to reach the desired constant state, vi) use humidity nozzle 20 to increase the relative humidity 22 to the desired value, adding moisture as required to maintain the desired value, vii) ceasing the use of humidity nozzle 20 will result a decrease in relative humidity 22, viii) after reaching the lower desired relative humidity 22 value, moisture can be added with humidity nozzle 20 to maintain this lower bound value, ix) repeat the process from step 'vi' for humidity cycles. During the aforementioned process the air state is continuously monitored to ensure constant air temperature 21.

CONCLUSIONS

Although embodiments of this disclosed invention have been described in detail, it will be understood that these embodiments are shown by way of illustration and not as limitations of the invention. Equivalents to the specific procedures and embodiments described herein will be identified and determined through routine experimentation and experimental calibration by those skilled in the art. Variations and modifications to produce such equivalents may be employed within the scope of the disclosed invention as described in the claims.

Methods described herein are in terms of the current embodiments, those skilled in the art will be able to ascertain that variation to the methods and steps or in the sequence of steps may be applied. Such variations apparent to those skilled in the art should not deviate from the spirit and scope of the disclosed invention as described in the claims.

The subject invention includes, but is not limited to, the following exemplified embodiments.

Embodiment 1. A centrifuge environmental chamber comprising:
a frame of suitable strength to be used in a centrifuge disposed on top of a strongbox having at least one channel for air flow with inflow and outflow ends on opposite sides of the channel;
fans disposed at the inflow and outflow ends to induce air circulation;
cooling units comprising any cooling elements capable of lowering air temperature disposed in the channel in the path of the air flow; and
heating units comprising any heating elements capable of raising air temperature disposed in the channel in the path of the air flow:

Embodiment 2. The centrifuge environmental chamber of embodiment 1, wherein the fans are installed to allow for air to flow in opposite directions through the channel.

Embodiment 3. The centrifuge environmental chamber of embodiment 1, further comprising a humidity nozzle capable of creating atomized mist water vapor, in accordance with relevant centrifuge scaling laws, to permit change in a relative humidity of an air state.

Embodiment 4. The centrifuge environmental chamber of embodiment 1, further comprising rain nozzles capable of creating a fine spray of water droplets, in accordance with relevant centrifuge scaling laws, to permit simulation of rainfall conditions.

Embodiment 5. The centrifuge environmental chamber of embodiment 1, further comprising ultraviolet (UV), infrared (IR) and visible lighting to produce an irradiance spectrum and permit simulation of solar radiation as a boundary condition.

Embodiment 6. The centrifuge environmental chamber of embodiment 1, wherein the centrifuge environmental chamber is securely fastened to the strongbox and sealed and insulated to ensure an adiabatic system.

Embodiment 7. The centrifuge environmental chamber of embodiment 1, wherein the centrifuge environmental chamber further comprises an instrumentation module, sensors and software that continuously measures one or more variables relevant to the air state while the centrifuge environmental chamber is in flight, and wherein the sensors comprise:
a relative humidity sensor;
a temperature sensor; and
a wind speed sensor (Anemometer); and, optionally,
a solar radiation sensor (Pyranometer).

Embodiment 8. An apparatus for a centrifuge environmental chamber, comprising:
a model strongbox including a model space;
an airflow channel configured to allow air flow from the model space through the channel and back to the model space; and
a humidity nozzle placed in the model space.

Embodiment 9. The apparatus for the centrifuge environmental chamber of embodiment 8, wherein the humidity nozzle provides water vapor.

Embodiment 10. The apparatus for the centrifuge environmental chamber of embodiment 9, wherein the water vapor provided by the humidity nozzle has a mean drop size less than 30 µm.

Embodiment 11. The apparatus for the centrifuge environmental chamber of embodiment 10, wherein the water vapor provided by the humidity nozzle has a mean drop size of 6 µm.

Embodiment 12. The apparatus for the centrifuge environmental chamber of embodiment 8, further comprising a solid state heating unit that raises the temperature of the air in the airflow channel.

Embodiment 13. The apparatus for the centrifuge environmental chamber of embodiment 12, wherein the heating unit includes a finned strip aluminum heater.

Embodiment 14. The apparatus for the centrifuge environmental chamber of embodiment 8, further comprising a cooling unit that lowers the temperature of the air in the airflow channel.

Embodiment 15. The apparatus for the centrifuge environmental chamber of embodiment 14, wherein the cooling unit includes finned heat sinks in the airflow channel and heat dissipating heat sinks placed on an outside of the centrifuge environmental chamber.

Embodiment 16. The apparatus for the centrifuge environmental chamber of embodiment 15, wherein the cooling unit includes Peltier plates between the finned heat sinks and the heat dissipating heat sinks.

Embodiment 17. The apparatus for the centrifuge environmental chamber of embodiment 8, further comprising a first fan and a second fan disposed at opposite ends of the airflow channel, wherein the fans pull the air from the model space and push the air through a sealed channel to the model space.

Embodiment 18. The apparatus for the centrifuge environmental chamber of embodiment 17, wherein air in the airflow channel contacts a heating unit and a cooling unit.

Embodiment 19. The apparatus for the centrifuge environmental chamber of embodiment 18, further comprising directional air scoops disposed on the first and second fans.

Embodiment 20. The apparatus for the centrifuge environmental chamber of embodiment 8, further comprising a rain nozzle facing the model space.

Embodiment 21. The apparatus for the centrifuge environmental chamber of embodiment 8, further comprising first two I-beams disposed along the airflow channel and a second I-beam disposed between the first two I-beams.

Embodiment 22. The apparatus for the centrifuge environmental chamber of embodiment 21, further comprising flat plates fastening the heating unit and the cooling unit to the first two I-beams and the second I-beam.

Embodiment 23. The apparatus for the centrifuge environmental chamber of embodiment 22, wherein the humidity nozzle faces the model space.

Embodiment 24. A method for testing a centrifuge environmental chamber, comprising:
preparing an environmental chamber fastened to a model strongbox;
placing the environmental chamber on a centrifuge swing arm;

spinning the environmental chamber to a selected centrifuge acceleration level;

measuring an atmospheric state in a model space of the model strongbox; and controlling a humidity nozzle of the environmental chamber such that the atmospheric state reaches a desired atmospheric condition.

Embodiment 25. The method of embodiment 24, further comprising circulating air in the model space through an airflow channel of the environmental chamber.

Embodiment 26. The method of embodiment 25, wherein the air passing through the airflow channel is heated by a heating unit of the environmental chamber.

Embodiment 27. The method of embodiment 26, wherein the air passing through the airflow channel is cooled by a cooling unit of the environmental chamber.

Embodiment 28. The method of embodiment 27, wherein fans at both ends of the airflow channel pull air from the model space, feed the air into the airflow channel, and push back the air in the airflow channel into the model space.

Embodiment 29. The method of embodiment 28, wherein the fans are variable speed fans inducing different wind speed.

Embodiment 30. The method of embodiment 24, further comprising providing radiation heating by at least one of an infrared light, an ultraviolet light, and a visible lighting.

What is claimed is:

1. A centrifuge environmental chamber comprising:
a frame for a centrifuge disposed on top of a strongbox having at least one channel for air flow with inflow and outflow ends on opposite sides of the channel;
a plurality of fans disposed at the inflow end or the outflow end, being configured in-flight to cause air to flow either in a clockwise direction or a counterclockwise direction through the channel;
cooling units comprising cooling elements capable of lowering air temperature and disposed in the channel in a path of the air flow;

heating units comprising heating elements capable of raising air temperature and disposed in the channel in the path of the air flow; and a humidity nozzle comprising a humidity control and a temperature control configured to generate atomized mist water vapor to maintain a constant relative humidity of the air during a change of air temperature, such that when the centrifuge environmental chamber is under a gravitational acceleration equal to 1 g, the atomized mist water vapor generated has a mean diameter smaller than or equal to 6 μm; and when the gravitational acceleration of the centrifuge environmental chamber is greater than 1 g and increased, the mean diameter of the atomized mist water vapor scales to be greater than 6 μm and increased.

2. The centrifuge environmental chamber of claim 1, further comprising rain nozzles capable of creating a fine spray of water droplets with mean drop diameters ranging from 30 μm to 60 μm to permit simulation of rainfall conditions.

3. The centrifuge environmental chamber of claim 1, further comprising ultraviolet (UV), infrared (IR) and visible lighting to produce an irradiance spectrum and permit simulation of solar radiation as a boundary condition.

4. The centrifuge environmental chamber of claim 1, wherein the centrifuge environmental chamber further comprises an instrumentation module, sensors and software that continuously measure one or more variables relevant to an air state while the centrifuge environmental chamber is in flight, and wherein the sensors comprise:

a relative humidity sensor;

a temperature sensor;

a wind speed sensor; and a solar radiation sensor.

5. The centrifuge environmental chamber of claim 1, wherein the plurality of fans comprises variable speed fans controlled in-flight to induce different wind speeds.

6. The centrifuge environmental chamber of claim 1, wherein the centrifuge environmental chamber is configured to run without cessation during centrifuge testing.

7. An apparatus for a centrifuge environmental chamber, comprising:

a model strongbox including a model space;

an airflow channel configured to pull air from the model space and to push the air back to the model space;

a plurality of fans disposed at an inflow end of the airflow channel or an outflow end of the airflow channel, being configured in-flight to cause air to flow either in a clockwise direction or a counterclockwise direction through the airflow channel; and a humidity nozzle comprising a humidity control and a temperature control configured to generate atomized mist water vapor to maintain a constant relative humidity of the air during a change of air temperature, such that when the centrifuge environmental chamber is under a gravitational acceleration equal to 1 g, the atomized mist water vapor generated has a mean diameter smaller than or equal to 6 μm; and when the gravitational acceleration of the centrifuge environmental chamber is greater than 1 g and increased, the mean diameter of the atomized mist water vapor scales to be greater than 6 μm and increased.

8. The apparatus for the centrifuge environmental chamber of claim 7, further comprising a heating unit that raises a temperature of the air in the airflow channel.

9. The apparatus for the centrifuge environmental chamber of claim 8, wherein the heating unit includes an aluminum-finned strip heater.

10. The apparatus for the centrifuge environmental chamber of claim 7, further comprising a cooling unit that lowers a temperature of the air in the airflow channel.

11. The apparatus for the centrifuge environmental chamber of claim 10, wherein the cooling unit includes finned heat sinks in the airflow channel and heat dissipating heat sinks placed on an outside of the centrifuge environmental chamber.

12. The apparatus for the centrifuge environmental chamber of claim 11, wherein the cooling unit includes Peltier plates between the finned heat sinks and the heat dissipating heat sinks.

13. The apparatus for the centrifuge environmental chamber of claim 7, wherein the plurality of fans comprises a first fan and a second fan disposed at the inflow and outflow ends of the airflow channel, respectively, and wherein the fans pull the air from the model space and push the air through a sealed channel to the model space.

14. The apparatus for the centrifuge environmental chamber of claim 13, wherein the air in the airflow channel contacts a heating unit and a cooling unit.

15. The centrifuge environmental chamber of claim 14, wherein when the air flows in a counter-clockwise direction, the heating units are cooled by the cooling units; then, when the direction is changed to clockwise direction, cold air is generated from the cooling units to be directly blown into the model space; and then, when the direction is changed again during heating, hot air is blown from the heating units into the model space without having to flow through the channel.

16. The apparatus for the centrifuge environmental chamber of claim 13, further comprising directional air scoops disposed on the first and second fans.

17. The apparatus for the centrifuge environmental chamber of claim 7, further comprising first two I-beams disposed along the airflow channel and a second I-beam disposed between the first two I-beams.

18. The apparatus for the centrifuge environmental chamber of claim 17, further comprising flat plates fastening the heating unit and the cooling unit to the first two I-beams and the second I-beam, respectively.

19. The apparatus for the centrifuge environmental chamber of claim 7, wherein the humidity nozzle faces the model space.

20. A method for testing a centrifuge environmental chamber, comprising:
preparing an environmental chamber fastened to a model strongbox;
placing the environmental chamber on a centrifuge swing arm;

circulating air in a model space of the model strongbox through an airflow channel of the environmental chamber, placing a plurality of fans at an inflow end or an outflow end of the airflow channel, the fans being configured in-flight to cause air to flow either in a clockwise direction or a counterclockwise direction through the airflow channel;

spinning the environmental chamber to a selected centrifuge acceleration level;

measuring an atmospheric state in a model space of the model strongbox; and controlling a humidity nozzle to generate atomized mist water vapor, the humidity nozzle capable of maintaining a constant relative humidity of the air during a change of air temperature, such that when the centrifuge environmental chamber is under a gravitational acceleration equal to 1 g, the atomized mist water vapor generated has a mean diameter smaller than or equal to 6 μm; and when the gravitational acceleration of the centrifuge environmental chamber is greater than 1 g and increased, the mean diameter of the atomized mist water vapor scales to be greater than 6 μm and increased.

21. The method of claim 20, wherein the air circulating in the airflow channel is heated by a heating unit of the environmental chamber.

22. The method of claim 20, wherein the air circulating in the airflow channel is cooled by a cooling unit of the environmental chamber.

23. The method of claim 20, wherein the fans placed at the inflow and outflow ends of the airflow channel pull air from the model space, feed the air into the airflow channel, and push the air in the airflow channel back into the model space.

24. The method of claim 23, wherein the fans are variable speed fans controlled in-flight to induce different wind speeds.

25. The method of claim 20, further comprising providing radiation heating by at least one of an infrared light, an ultraviolet light, and a visible lighting.

* * * * *